(12) United States Patent
Koga

(10) Patent No.: US 6,218,411 B1
(45) Date of Patent: Apr. 17, 2001

(54) THERAPEUTICS FOR DIABETIC COMPLICATIONS

(75) Inventor: Hiroshi Koga, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/485,297

(22) PCT Filed: Aug. 7, 1998

(86) PCT No.: PCT/JP98/03525

§ 371 Date: Feb. 8, 2000

§ 102(e) Date: Feb. 8, 2000

(87) PCT Pub. No.: WO99/07411

PCT Pub. Date: Feb. 18, 1999

(30) Foreign Application Priority Data

Aug. 8, 1997 (JP) ................................................ 9-214659

(51) Int. Cl.$^7$ ............................ A61K 31/44; A61K 31/40

(52) U.S. Cl. ............................ 514/355; 514/353; 514/422

(58) Field of Search ..................................... 514/355, 353, 514/422

(56) References Cited

U.S. PATENT DOCUMENTS 4,822,808 * 4/1989 Iida et al. ............................. 514/355

* cited by examiner

Primary Examiner—Theodore J. Criares
Assistant Examiner—Jennifer Kim
(74) Attorney, Agent, or Firm—Browdy and Neimark

(57) ABSTRACT

An agent for treating or ameliorating diabetic complications which contains at least one potassium channel activator as an active ingredient. The drug is expected to show a therapeutic or ameliorating action on diabetic complications such as retinopathy, neuropathy, nephropathy, peripheral circulation disorders, and skin ulcerations; it also proves effective in preventing, ameliorating, alleviating and gaining recovery from various symptoms and abnormalities caused by those diseases, as exemplified by blindness, proteinurea, pain, numbness, psychroesthesia, intermittent claudication and gangrene.

7 Claims, No Drawings

THERAPEUTICS FOR DIABETIC COMPLICATIONS

TECHNICAL FIELD

This invention relates to agents for treating or ameliorating diabetic complications that are characterized by containing at least one potassium channel activator as an active ingredient. More particularly, the invention relates to treating or ameliorating agents that contain nicorandil, pinacidil, cromakalim or other potassium channel activators as an active ingredient and which are effective against diabetic complications such as retinopathy, neuropathy, nephropathy, peripheral circulation disorders and skin ulcerations.

BACKGROUND ART

Diabetes mellitus is one of the diseases that have recently seen the most dramatic increase in the number of patients in Japan and five to six million patients, including those undiagnosed, are estimated to exist. The number of patients with diabetes mellitus is almost comparable to those of patients with hyperlipidemia and hypertension. The cases of diabetes mellitus will certainly continue to increase in the years to come and may even double or triple sometime around 2010.

For the treatment of diabetes mellitus, two things are the most important, i.e., effective control of blood glucose levels and retarding the development and progression of complications such as retinopathy, neuropathy, nephropathy, peripheral circulation disorders and skin ulcerations.

The incidence of diabetic complications increases with time, or the number of years the patient has been suffering from diabetes mellitus. For example, under normal control of blood glucose, about one half of the patients with diabetes mellitus develop retinopathy in 10 years of affliction and in 20 years, almost all cases develop retinopathy, which is currently the leading cause of blindness (in each year, about 5000 people lose vision in retinopathy). Statistically, the incidence of neuropathy is substantially the same. About 20% of the patients with diabetes develop nephropathy in 10 years and about 30% of the patients starting renal dialysis have already suffered from diabetic nephropathy, which is one of the major reasons for the initiation of dialysis (in each year, about 6000 diabetic patients start renal dialysis). From now on, increasing number of cases that start renal dialysis will be estimated to be attributable to diabetic nephropathy. Peripheral circulation disorders occur in 10–40% of diabetic patients and they tend to worsen, which is one of the major reasons for amputations of the lower extremities.

In Japan, about one and a half million people are estimated to be suffering from diabetic complications. According to the Epidemiologic Study Report of the Japanese Ministry of Health and Welfare (1990), diabetic complications in Japan comprised 170,000 nephropathy cases, 600,000 retinopathy cases, 540,000 neuropathy cases and 230,000 cases of arteriosclerotic diseases. As of today, these numbers of the respective cases have certainly increased to higher levels.

Abnormal blood circulation in the retina of the eye has been pointed out as a cause of diabetic retinopathy. As a result of the measurement of circulation in the retina of patients at varying stages of retinopathy, it has been reported that the amount of circulation decreased with the progress of retinopathy. It has also been reported the distribution of blood vessels in the retina is abnormal. In short, poor circulation due to disorders in retinal small blood vessels causes chronic lack of oxygen and nutrients in the retinal tissue and this would induce pathological changes in diabetic retinopathy.

A predominant finding with diabetic neuropathy is the segmental demyelination of Schwann cells. The basement membrane thickening and occlusion of neurotrophic vessels have been recognized in patients with diabetic neuropathy. These vascular disorders would cause poor circulation in nerves, eventually inducing neuropathy.

Diabetic nephropathy is caused by disorders in renal glomerular vessels. Soon after the development of diabetes mellitus, the filtration rate of glomeruli is found to increase. After several years after the onset of the disease, basement membrane thickening and the growth of mesangium occur and, as a result, the vessel walls thicken and the bore of vessels becomes narrower, causing circulation disorder. These changes mostly occur in afferent glomerular arterioles and are seldom in efferent glomerular arterioles. Subsequently, these changes develop into glomerulosclerosis and, following the increase in blood pressure and the occurrence of proteinurea, further develop into nephropathy.

Diabetic peripheral circulation disorders are diseases that occur primarily in the peripheral vessels in the extremities to present with ischemic conditions by way of their constriction and occlusion. In most of these cases, occlusion occurs in more peripheral vessels and is prone to become serious, even advancing to a stage where amputation of the lower extremities is necessary.

Turning back to potassium channel activators, they are drugs that open potassium channels in cells, thereby relaxing the smooth muscle to display various actions. It is known that if applied to blood vessels, potassium channel activators increase the blood circulation by relaxing the vessels (see, for example, Japanese Patent Domestic Announcement No. 501010/1988). However, it has not been known at all that potassium channel activators are effective against diabetic complications such as retinopathy, neuropathy, nephropathy, peripheral circulation disorders and skin ulcerations.

It has been proved that the development and progression of diabetic complications can be checked to some extent by tight control of blood glucose levels. However, tight control of glucose levels can only be accomplished by intensive insulin therapy and it is not a practical method of treatment for patients with NIDDM (non-insulin-dependent diabetes mellitus) who account for the greater part of diabetic patients. Even if tight control of blood glucose is possible as in patients with IDDM (insulin-dependent diabetes mellitus), it can retard, but not prevent, the development of complications. In addition, tight control of blood glucose levels is hardly effective in curing complications or checking their progression if they are at an advanced stage. Given these limitations on the efforts to check the development and progression of complications solely by controlling blood glucose, a drug is desired that is capable of directly preventing the development and progression of diabetic complications. As of today, very few drugs meet this requirement and there is a very strong need to develop a truly effective drug which if used either alone or in combination with a hypoglycemic agent, can check the development and progression of diabetic complications.

DISCLOSURE OF INVENTION

In view of this situation, the present inventors made intensive studies and found that potassium channel openers have an outstanding therapeutic or ameliorating action on diabetic complications such as neuropathy, nephropathy, peripheral circulation disorders and skin ulcerations. The present invention has been accomplished on the basis of this finding.

Various potassium channel activators may be used in the invention without any particular limitations as long as they have the ability to open potassium channels and exhibit the resulting vasodilating or circulation enhancing action. Examples include nicorandil, pinacidil, minoxidil, cromakalim, levcromakalim, bimakalim, celikalim, aprikalim, Ro31-6930, EMD-57283, SDZ-PCO-400, Y-27152, RWJ-26629, YM-934, YM-099, KRN-2391, TCV-295, AL0671, KC-399, KC-515, and the compounds described in International Publications WO92/14439, WO93/15068, WO94/04521 and WO94/25021, as well as pharmaceutically acceptable salts thereof, with nicorandil and its pharmaceutically acceptable salts being preferred.

The potassium channel activators used in the invention are expected to show a therapeutic or ameliorating action on diabetic complications such as retinopathy, neuropathy, nephropathy, peripheral circulation disorders and skin ulcerations; they also prove effective in preventing, ameliorating, alleviating and gaining recovery from various symptoms and abnormalities caused by resulting those diseases, as exemplified by blindness, proteinurea, pain, numbness, psychroesthesia, intermittent claudication and gangrene.

BEST MODE FOR CARRYING OUT THE INVENTION

The agent of the invention for treating or ameliorating diabetic complications may be administered to the living body either orally or parenterally such as by intrarectal, subcutaneous, intraspinal, intramuscular, intravenous, intra-arterial, percutaneous and ophthalmic routes. Oral, intravenous and percutaneous administrations are preferred.

When administering the potassium channel activators of the invention to the living body, they are preferably formulated into appropriate pharmaceutical dosage forms including, for example, tablets, powders, granules, fine granules, pills, capsules, lozenges, chewables, liquids, emulsions, suspensions, suppositories, syrups, lotions, ointments and cataplasms. Formulating into these dosage forms can be accomplished using any suitable carriers, vehicle additives and so forth that are pharmaceutically acceptable.

Liquids are a preferred dosage form for intravenous administration of the agent of the invention for treating or ameliorating diabetic complications. To prepare liquids, purified water, physiological saline, alcohols such as ethanol, propylene glycol, glycerin and polyethylene glycol, and solvents such as triacetin may be used. The liquids may further contain auxiliary agents such as antiseptics, moistening agents, emulsifiers, dispersing agents and stabilizers. The drug of the invention may also be administered as a suspension.

To prepare solid drugs such as tablets, pills, powders, granules, fine granules, lozenges and chewables, conventional procedures may be employed after adding carriers such as sodium bicarbonate, calcium carbonate, starch, sucrose, mannitol and carboxymethylcellulose, and additives such as calcium stearate, magnesium stearate and glycerin. If desired, enteric coats may be formed by spraying solutions, in either organic solvents or water, of enteric coating substances such as cellulose acetate phthalate, hydroxypropyl methylcellulose phthalate, polyvinyl alcohol phthalate, styrene-maleic anhydride copolymer and methacrylic acid-methyl methacrylate copolymer; the resulting preparation is an enteric drug. Other pharmaceutically acceptable carriers include auxiliary agents, fragrances, stabilizers and antiseptics that may be used as required.

The preparations mentioned above may be formulated by the methods described in Japanese Patent Public Disclosure Nos. 145659/1982, 39618/1993, 143316/1986, 149630/1987, 161727/1987, 252722/1987, 252723/1987, 270624/1988, etc. Further details are given below with nicorandil taken as an example. To prepare tablets, nicorandil or its salts may be incorporated in organic acids such as fumaric acid, oxalic acid, salicylic acid, tartaric acid and glutaric acid, together with one or more of saturated higher aliphatic acids such as stearic acid and palmitic acid that are solid at room temperature or saturated higher alcohols such as cetyl alcohol and stearyl alcohol; alternatively, nicorandil or its salts may be mixed with fumaric acid and/or DL-tryptophan.

To prepare injections, nicorandil or its salts may be incorporated in alkali metal salts of organic acids such as citric acid, fumaric acid, oxalic acid, malonic acid, maleic acid, and tartaric acid; the thus prepared injections are of a non-solution type. In the case of preparing injections, pharmaceutically acceptable and conventional carriers are preferably incorporated, as exemplified by vehicles, disintegrators, lubricants, binders, scents, coloring agents, and so forth. Exemplary carriers include lactose, corn starch, mannitol, kaolin, crystalline cellulose, hydroxypropyl cellulose, hydroxypropyl methylcellulose, carboxylmethylcellulose, carboxymethylcellulose calcium, talc, croscarmellose sodium, anhydrous calcium hydrogenphosphate, calcium carbonate, calcium citrate, calcium stearate, magnesium stearate, and so forth.

The dose of the agent of the invention for treating or ameliorating diabetic complications varies with the drug type, the sex of the patient, his or her physique, constitution, age, symptoms, dosage form, etc.; typically, a suitable dose may be selected from a range of 0.1 $\mu$g–1 g, preferably from a range of 1 $\mu$g–100 mg, per day. If nicorandil is used as a potassium channel activator, a suitable dose may be selected from a range of 10–100 mg, preferably from a range of 15–60 mg, per day. The frequency of administration varies with the symptoms of the patient or the dosage form and one to several times a day is suitable.

EXAMPLES

The following examples are provided for the purpose of further illustrating the invention but are in no way to be taken as limiting.

Example 1
Action of Nicorandil on Neuropathy and Nephropathy

Ten-week old Wistar rats were administered streptozocin (hereunder abbreviated as STZ); 24 hours later, the tip of their tails was severed to take a blood sample and its glucose level was measured in the usual manner; rats having glucose levels of 300 mg/dl or more were selected and subjected to an experiment. The nerve conduction velocity before administration of a test substance was measured in the usual manner and the rats were divided into groups, each consisting of 6 animals, on the basis of the measured nerve conduction velocity. Starting on the next day, a test substance was administered; on the last day of administration, glucose levels were measured by the same method as described above and 6-hour urine samples were taken to calculate the excretion of proteinurea. On the day after the last administration, the nerve conduction velocity and the blood circulation within the sciatic nerve were measured (see Diabetologia, 38, 914–918 (1995); Nanuyu-Schmiedeberg's Arch Pharmacol., 351, 630–635(1995).

Nicorandil was used as the test substance; it was suspended in 0.3% CMC-Na to make an administration volume of 5 ml/kg. The dose of nicorandil was 3 mg/kg, 10 mg/kg or 30 mg/kg; it was repeatedly administered perorally for 5 weeks on a twice-a-day basis. Two control groups were designed, one being a group of STZ administered diabetic rats and the other being a normal group of rats that were not administered STZ; both groups were repeatedly administered 5 ml/kg of 0.3% CMC-Na perorally for 5 weeks on a twice-a-day basis.

Nerve conduction velocity measurement was performed by the following method: rats under pentobarbital anesthesia were pierced with a needle electrode for distal stimulation near the right sciatic nerve, a needle electrode for proximal stimulation near the ipsilateral Achilles tendon and a third needle electrode for measurement near the sole of the ipsilateral foot; the distal and proximal stimulating electrodes were connected to an electrical stimulator to perform stimulation with rectangular waves (0.5 Hz, 0.1 msec, submax voltage); the induced potential was derived from the measuring electrode and input to a high-speed data processor through a bioelectrical amplifier; the arithmetic mean of 10 measurements was recorded to calculate the difference in nerve conduction velocity between distal and proximal sites.

To measure the blood circulation within the sciatic nerve, the femoral portion of each rat was incised under anesthesia with pentobarbital to have the sciatic nerve become exposed and a platinum electrode was pierced into the nerve, followed by measurement by the hydrogen gas clearance method. Throughout the measurement, the rats were warmed so that their body temperature remained at 37–38° C.

In the STZ-administered control group, both the nerve conduction velocity and the blood circulation in the sciatic nerve decreased compared to the non-STZ-administered control group. These phenomena were improved in the nicorandil administered group. In the STZ-administered control group, the excretion of proteinurea increased compared to the non-STZ-administered control group; this phenomenon was also improved in the nicorandil administered group.

Example 2

Action of KC-515 on Neuropathy and Nephropathy

An experiment was conducted as in Example 1, except that nicorandil was replaced by KC-515 [2,2-bis(fluoromethyl)-N-(2-cyanoethyl)-6-pentafluoroethyl-2H-1-benzopyran-4-carboxamide, as synthesized by the method described in International Publication WO93/15068].

The test substance, KC-515, was suspended in 0.3% CMC-Na to make an administration volume of 5 ml/kg. The dose of KC-515 was 10 $\mu$g/kg, 30 $\mu$g/kg or 100 $\mu$g/kg; it was repeatedly administered perorally for 5 weeks on a once-a-day basis. Two control groups were designed, one being a group of STZ administered diabetic rats and the other being a normal group of rats that were not administered STZ; both groups were repeatedly administered 5 ml/kg of 0.3% CMC-Na perorally for 5 weeks on a once-a-day basis.

The nerve conduction velocity and the blood circulation in the sciatic nerve were measured by the same methods as applied in Example 1.

In the STZ-administered control group, both the nerve conduction velocity and the blood circulation in the sciatic nerve decreased compared to the non-STZ-administered control group. These phenomena were improved in the KC-515 administered group. In the STZ-administered control group, the excretion of proteinurea increased compared to the non-STZ-administered control group; this phenomenon was also improved in the KC-515 administered group.

Example 3

Action of Nicorandil on Peripheral Circulation Disorder (Adrenaline-Ergotamine Model)

Wistar male rats (12–13 weeks old) were fixed without anesthesia; thereafter, they were administered subcutaneously with 0.1 mg of adrenaline at two sites 6 cm distant from the tip of the tail; at the same time, they were administered subcutaneously with 5 mg/kg of ergotamine on the back. In order to know the length of a lesion in the tail, the positions 5, 10 and 15 cm distant from the tip of the tail were marked. A solvent and nicorandil were administered perorally both one hour before and three hours after the administration of adrenaline and ergotamine. Starting on the next day, the solvent and nicorandil were administered perorally for 13 days on a twice-a-day basis. The progress of the lesion was evaluated 14 days after the administration of adrenaline and ergotamine by measuring the maximum length of the affected area.

Nicorandil was suspended in 0.3% CMC-Na to make an administration volume of 5 ml/kg; the dose of nicorandil was 3 mg/kg, 10 mg/kg or 30 mg/kg. The control group was administered 5 ml/kg of 0.3% CMC-Na. The results are shown in Table 1.

TABLE 1

Action of Nicorandil in Models with Adrenaline-Ergotamine Induced Peripheral Circulation Disorder

|  | No. of animals | Length of gangrene, cm |
|---|---|---|
| Control group [0.3% CMC—Na (5 ml/kg)] | 9 | 13.8 ± 0.5 |
| Nicorandil (3 mg/kg) group | 9 | 13.3 ± 0.7 |
| Nicorandil (10 mg/kg) group | 9 | 11.8 ± 0.6* |
| Nicorandil (30 mg/kg) group | 9 | 9.2 ± 0.5** |

*,**Statistically significant over the control group at $p < 0.05$(*) and $p < 0.01$(**) (in Student's t test)

As in clear from Table 1, nicorandil is effective against peripheral circulation disorders in a dose-dependent manner.

Example 4

Action of Nicorandil on Peripheral Circulation Disorder (Laurate Model)

Wistar male rats (12–13 weeks old) were anesthetized by intraperitoneal administration of 40 mg/kg of pentobarbital sodium. After being fixed in a supine position, the rats were administered 0.15 ml of a lauric acid solution (10 mg/ml) in the right femoral artery. Bleeding was arrested by dripping a quick-acting adhesive (ARON-ALPHAR$^{RT}$) and the incised area was sutured. A solvent and nicorandil were administered perorally both before one hour and three hours after the administration of lauric acid. Starting on the next day, the solvent and nicorandil were administered perorally for 9 days on a twice-a-day basis. The progress of the lesion was evaluated 10 days after the administration of lauric acid according to the following criteria;

0: normal
1: gangrene, mummification or shedding of nails
2: gangrene, mummification or shedding of fingers
3: gangrene, mummification or shedding up to one half of the instep
4: gangrene, mummification or shedding of the entire instep Nicorandil was suspended in 0.3% CMC-Na to make an administration volume of 5 ml/kg; the dose of nicorandil was 3 mg/kg, 10 mg/kg or 30 mg/kg. The control group was administered 5 ml/kg of 0.3% CMC-Na. The results are shown in Table 2.

TABLE 2

Action of Nicorandil in Models with Laurate Induced Peripheral Circulation Disorder

| | No. of animals | Length of lesion, cm |
|---|---|---|
| Control group [0.3% CMC—Na (5 ml/kg)] | 10 | 3.3 ± 0.4 |
| Nicorandil (3 mg/kg) group | 10 | 2.5 ± 0.5 |
| Nicorandil (10 mg/kg) group | 9 | 2.2 ± 0.6 |
| Nicorandil (30 mg/kg) group | 9 | 1.6 ± 0.6* |

*Statistically significant over the control group at $p < 0.05$ (in Mann-Whitney U test)

As is clear from Table 2, nicorandil is effective against peripheral circulation disorders in a dose-dependent manner.

Example 5

Action of KC-515 on Peripheral Circulation Disorders (Adrenaline-Ergotamine Model)

An experiment was performed as in Example 3. KC-515 was synthesized by the method described in International Publication WO93/15068 and submitted to the experiment. A solvent and KC-515 were administered perorally one hour before the administration of adrenaline-ergotamine; starting on the next day, they were administered perorally for 13 days on a once-a-day basis.

KC-515 was suspended in 0.3% CMC-Na to make an administration volume of 5 ml/kg; the dose of KC-515 was 10 μg/kg, 30 μg/kg or 100 μg/kg. The results are shown in Table 3.

TABLE 3

Action of KC-515 in Models with Adrenaline-Ergotamine Induced Peripheral Circulation Disorder

| | No. of animals | Length of gangrene, cm |
|---|---|---|
| Control group [0.3% CMC—Na (5 ml/kg)] | 9 | 13.8 ± 0.5 |
| KC-515 (10 μg/kg) group | 9 | 11.5 ± 0.4** |
| KC-515 (30 μg/kg) group | 9 | 11.4 ± 0.4** |
| KC-515 (100 μg/kg) group | 9 | 11.4 ± 0.4** |

**Statistically significant over the control group at $p < 0.01$ (in Student's t test)

As is clear from Table 3, KC-515 is effective against peripheral circulation disorders.

Industrial Applicability of the Invention

The potassium channel activators used in the invention are expected to show a therapeutic or ameliorating action on diabetic complications such as retinopathy, neuropathy, nephropathy, peripheral circulation disorders and skin ulcerations; they also prove effective in preventing, ameliorating, alleviating and gaining recovery from various symptoms and abnormalities caused by those diseases, as exemplified by blindness, proteinurea, pain, numbness, psychroesthesia, intermittent claudication and gangrene.

What is claimed is:

1. A method for treating at least one diabetic complication in a patient suffering from diabetes mellitus comprising administering to said patient an effective amount of at least one potassium channel activator as an active ingredient.

2. The method according to claim 1, wherein the potassium channel activator is nicorandil or a pharmaceutically acceptable salt.

3. The method according to claim 1, wherein the diabetic complication is retinopathy.

4. The method according to claim 1, wherein the diabetic complication is neuropathy.

5. The method according to claim 1, wherein the diabetic complication is nephropathy.

6. The method according to claim 1, wherein the diabetic complication is a peripheral circulation disorder.

7. The method according to claim 1, wherein the diabetic complication is skin ulceration.

* * * * *